United States Patent
Gormsen et al.

(10) Patent No.: US 7,883,711 B2
(45) Date of Patent: Feb. 8, 2011

(54) USE OF POLYPEPTIDES HAVING ANTIMICROBIAL ACTIVITY

(75) Inventors: Erik Gormsen, Virum (DK); Debbie Yaver, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/282,429

(22) PCT Filed: Mar. 20, 2007

(86) PCT No.: PCT/EP2007/052652

§ 371 (c)(1),
(2), (4) Date: Oct. 16, 2008

(87) PCT Pub. No.: WO2007/107573

PCT Pub. Date: Sep. 27, 2007

(65) Prior Publication Data

US 2009/0137474 A1     May 28, 2009

Related U.S. Application Data

(60) Provisional application No. 60/784,617, filed on Mar. 22, 2006, provisional application No. 60/816,242, filed on Jun. 23, 2006.

(51) Int. Cl.
*A61K 39/07*     (2006.01)
(52) U.S. Cl. .................. 424/246.1; 424/190.1; 435/32; 435/252.1
(58) Field of Classification Search ........................ None
See application file for complete search history.

(56) References Cited

PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Veith et al, Journal of Molecular Microbiology, vol. 7, No. 4, pp. 204-211 (2004).
Rey et al, GenBank, NC_006270, (2008).
Rey et al, Genome Biology, vol. 5, No. 10, pp. R77.
Veith et al, UniProtB/TrEMBL entry Q65CU4 (2004).
Rey et al, Database GenPept Accession AAU25737 (2006).

* cited by examiner

*Primary Examiner*—Jennifer E Graser
(74) *Attorney, Agent, or Firm*—Elias J. Lambiris

(57) ABSTRACT

The present invention relates to the use of polypeptides related to a *Bacillus licheniformis* polypeptide (amino acids 1-85 of SEQ ID NO: 2) as antimicrobial agents, for example in pharmaceutical applications, including veterinary applications, as well as for preservation, cleaning and disinfection of various surfaces, objects and substances. The polypeptides may in particular be used to treat textiles or laundry, e.g., in detergents, for reducing microbes on textile or laundry, and/or for odor reduction. The invention also relates to use of *Bacillus* strains producing these polypeptides as antimicrobial agents. Examples of microorganism inhibited by Lento are Gram positive bacterial strains, such as *Bacillus cereus*, and various species of *Corynebacterium, Enterococcus, Micrococcus, Streptococcus*, and *Staphylococcus*.

8 Claims, No Drawings

USE OF POLYPEPTIDES HAVING ANTIMICROBIAL ACTIVITY

CROSS-REFERENCE TO RELATED APPLICATIONS

This application is a 35 U.S.C. 371 national application of PCT/EP2007/052652 filed Mar. 20, 2007, which claims priority or the benefit under 35 U.S.C. 119 of U.S. provisional application Nos. 60/784,617 and 60/816,242 filed Mar. 22, 2006 and Jun. 23, 2006, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to the use of polypeptides related to a *Bacillus licheniformis* polypeptide (amino acids 1-85 of SEQ ID NO: 2) as antimicrobial agents, for example in pharmaceutical applications, including veterinary applications, as well as for preservation, cleaning and disinfection of various surfaces, objects and substances. The polypeptides may in particular be used to treat textiles/laundry, e.g., in detergents, for reducing microbes on textile and/or odor. The invention also relates to use of *Bacillus* strains producing these polypeptides as antimicrobial agents. The polypeptide having amino acids 1-85 of SEQ ID NO: 2 is herein designated "Lento".

BACKGROUND OF THE INVENTION

Background Art

GenPept accession no. YP_081375 is a hypothetical protein BL00275 from *Bacillus licheniformis* ATCC 14580. GenPept accession no. YP_081375 is identical to amino acids −41 to +85 of SEQ ID NO: 2 herein.

The nucleotide sequence encoding YP_081375 has Gen-Bank accession no. NC_006270. GenBank accession no. NC_006270 is identical to nucleotides 1-381 of SEQ ID NO: 1 herein.

The present inventors surprisingly found that polypeptides related to part of the *Bacillus licheniformis* hypothetical protein sequence, viz. amino acids 1-85 of SEQ ID NO: 2, have antimicrobial activity.

It is an object of the present invention to provide methods of using these antimicrobial polypeptides.

SUMMARY OF THE INVENTION

The present invention relates to the use of a polypeptide as an antimicrobial agent, wherein the polypeptide is selected from the group consisting of: (a) a polypeptide comprising an amino acid sequence which has a degree of identity to amino acids 1-85 of SEQ ID NO: 2 of at least 33%; (b) a polypeptide which is encoded by a nucleic acid sequence which hybridizes under low stringency conditions with (i) nucleotides 124-378 of SEQ ID NO: 1, (ii) a subsequence of (i) of at least 100 nucleotides, or (iii) a complementary strand of (i), or (ii); (c) a variant of the polypeptide having an amino acid sequence of amino acids 1-85 of SEQ ID NO: 2 comprising a substitution, deletion, extension, and/or insertion of one or more amino acids; (d) an allelic variant of (a) or (b); and (e) a fragment of (a), (b), (c), or (d).

The present invention in particular relates to the use of, and methods of using, such polypeptides as medicaments, for use in veterinary or human medicine, for therapy or prophylaxis, for treatment of microbial infections—as well as to pharmaceutical compositions comprising the polypeptides.

The invention in particular also relates to the use of, and methods of using, such polypeptides in detergents and detergent additives, for reducing the number of microbes and/or odor in textiles and laundry.

The invention also relates to the use of, and methods of using, such polypeptides (i) for cleaning and/or disinfection of a surface; (ii) for preventing or reducing microbial contamination of an object; and/or (iii) for preservation of a substance.

The invention also relates to antimicrobial compositions, detergent compositions, and pharmaceutical compositions comprising such polypeptides.

The invention furthermore relates to the use of *Bacillus* strains producing such polypeptides for the same purposes.

DETAILED DESCRIPTION OF THE INVENTION

The present invention relates to the use of a polypeptide as an antimicrobial agent, wherein the polypeptide is selected from the group consisting of: (a) a polypeptide comprising an amino acid sequence which has a degree of identity to amino acids 1-85 of SEQ ID NO: 2 of at least 33%; (b) a polypeptide which is encoded by a nucleic acid sequence which hybridizes under low stringency conditions with (i) nucleotides 124-378 of SEQ ID NO: 1, (ii) a subsequence of (i) of at least 100 nucleotides, or (iii) a complementary strand of (i), or (ii); (c) a variant of the polypeptide having an amino acid sequence of amino acids 1-85 of SEQ ID NO: 2 comprising a substitution, deletion, extension, and/or insertion of one or more amino acids; (d) an allelic variant of (a) or (b); and (e) a fragment of (a), (b), (c), or (d).

In what follows, the polypeptide for use according to the invention is referred to as "the polypeptide of the invention".

Antimicrobial Agent and Activity

The term "antimicrobial agent" is defined herein as a chemical compound such as a polypeptide or a chemical composition which has antimicrobial activity.

The term "antimicrobial activity" (or "antimicrobial effect") means a capability of killing and/or inhibiting growth of microbial cells. Examples of microbial cells are cells of microorganisms.

The term "microorganisms" include bacteria, protozoa, algae, fungi (including yeast), and virus.

Antimicrobial activity may, e.g., be bactericidal, bacteriostatic, fungicidal, fungistatic, and/or virucidal. The term "bactericidal" is to be understood as capable of killing bacterial cells; the term "bacteriostatic" as capable of inhibiting bacterial growth, i.e., inhibiting growing bacterial cells; the term "fungicidal" as capable of killing fungal cells; the term "fungistatic" as capable of inhibiting fungal growth, i.e., inhibiting growing fungal cells; and the term "virucidal" is to be understood as capable of inactivating virus.

In the context of the present invention the term "inhibiting growth of microbial cells" is intended to mean that the cells are in the non-growing state, i.e., that they are not able to propagate.

In particular embodiments the polypeptide of the invention is (i) capable of inhibiting bacterial growth, viz. bacteriostatic; and/or (ii) capable of killing bacterial cells, viz. bactericidal.

For purposes of the present invention antimicrobial activity may be determined by the growth inhibition assay of Example 3 herein, viz. the Minimum Inhibitory Concentration (MIC) assay, which is described by the NCCLS (National Committee for Clinical Laboratory Standards, in: Methods for Determining Bactericidal Activity of Antimicrobial Agents; Approved Guideline. National Committee for Clinical Laboratory Standards (M26-A), Vol. 19, 1999).

Briefly, the MIC is determined by inoculating serial two fold dilutions of the polypeptide in Mueller-Hinton Broth (MHB) with a culture of the actively growing microorganism and incubating at 35° C. MICs are determined after 24 hours of incubation and defined as the lowest concentration of the polypeptide with no visible growth.

For the present purposes antimicrobial activity against a certain microorganism species is acknowledged for compounds having a MIC value below 300 microgram/ml.

In particular embodiments, antimicrobial activity against a certain microorganism species is acknowledged herein for compounds having a MIC value of (i) below 290, 280, 270, or below 260 microgram/ml; (ii) below 250, 200, 150, 130, or below 100 micrograms/ml; (iii) below 75, 50, 25, 20, or below 16 micrograms/ml; and/or (iv) below 15, 14, 13, 12, 11, 10, 9, 8, 7, 6, 5, 4, 3, 2, or below 1 microgram/ml.

In still further particular embodiments antimicrobial activity against a certain microorganism species is acknowledged for compounds having a MIC value not higher than 128, 64, 32, 16, 8, 4, 2, or not higher than 1 microgram/ml.

In specific particular embodiments the polypeptide of the invention has antimicrobial activity against at least one of the following specific microorganism species and strains:

(i) *Bacillus cereus*, such as strain ATCC 4342, preferably with a MIC value not higher than 30 micrograms/ml, or not higher than 25, 20, 15, 10, 5, 4, 3, 2, or 1 microgram/ml;

(ii) *Corynebacterium jeikeium*, such as ATCC 43216 or ATCC 43734, preferably with a MIC value not higher than 30 micrograms/ml, or not higher than 25, 20, 15, 10, 5, 4, 3, or 2 microgram/ml, for strain ATCC 43216 in particular a MIC value below 1 microgram/ml, preferably below 0.5, 0.4, 0.3, or 0.2 microgram/ml;

(iii) *Enterococcus faecalis*, such as *Enterococcus faecalis* VRE, for example strain ATCC 51299, preferably with a MIC value not higher than 200 microgram/ml, or not higher than 150, 100, 90, 80, 70, or 64 micrograms/ml, preferably not higher than 30 micrograms/ml, or not higher than 25, 20, 15, 14, 13, 12, 11, 10, 9, or 8 micrograms/ml;

(iv) *Enterococcus faecium*, such as *Enterococcus faecium* ATCC 51559, preferably with a MIC value not higher than 25, 20, 15, 10, 9, 8, 7, 6, 5, or 4 micrograms/ml;

(v) *Micrococcus luteus*, such as ATCC 9341, preferably with a MIC value not higher than 30 microgram/ml, or not higher than 25, 20, 15, 10, 9, or 8 micrograms/ml;

(vi) *Staphylococcus aureus* ATCC 29213, preferably with a MIC value not higher than 100 microgram/ml, or not higher than 90, 80, 70, 65, or 64 micrograms/ml;

(vii) *Staphylococcus aureus* ATCC 29737, preferably with a MIC value not higher than 100 microgram/ml, or not higher than 80, 60, 50, or 40 micrograms/ml, preferably not higher than 35, 32, 30, 25, 20, 15, 10, 9, or 8 micrograms/ml;

(viii) *Staphylococcus epidermidis*, such as ATCC 12228, preferably with a MIC value not higher than 200 microgram/ml, or not higher than 190, 180, 170, 160, 150, 140, 130, or 128 micrograms/ml; and/or (ix) *Streptococcus pneumoniae*, such as *Streptococcus pneumoniae* PSRSP and *Streptococcus pneumoniae* TCRSP, for example ATCC 49619, ATCC 700671, ATCC 700676, and ATCC 700902, preferably with a MIC value not higher than 30 micrograms/ml, or not higher than 25, 20, 15, 10, 9, 8, 7, 6, 5, 4, 3, 2, or 1 microgram/ml, for strain ATCC 49619 in particular a MIC value not higher than 2 micrograms/ml, for strain ATCC 700671 in particular a MIC value not higher than 2 micrograms/ml, for strain 700676 in particular a MIC value not higher than 4 micrograms/ml, and for strain ATCC 700902 in particular a MIC value not higher than 8, or not higher than 7, 6, 5 or 4 micrograms/ml.

Above embodiments (i), (ii), (iii), (iv), (v), and (ix) constitute a preferred subgroup.

In the alternative, antimicrobial activity against a certain microorganism species is acknowledged for compounds having a MIC value below 1000, preferably below 900, 800, 700, 600, 500, or below 400 micrograms/ml.

In another alternative, antimicrobial activity may be determined according to the procedure described by Lehrer et al., Journal of Immunological Methods, Vol. 137 (2), pp. 167-174 (1991).

Antimicrobial activity may furthermore, alternatively and/or additionally, be determined by the Minimum Bactericidal Concentration (MBC) assay of Example 3 herein, which is described by the NCCLS (National Committee for Clinical Laboratory Standards, in: Methods for Determining Bactericidal Activity of Antimicrobial Agents; Approved Guideline. National Committee for Clinical Laboratory Standards (M26-A), Vol. 19, 1999).

Briefly, first the MIC is determined by inoculating serial two fold dilutions of the polypeptide in Mueller-Hinton Broth (MHB) with a culture of the actively growing microorganism and incubating at 35° C. MICs are determined after 24 hours of incubation and defined as the lowest concentration of the polypeptide with no visible growth. Next, to determine the MBC, 10 microliters from each well with no growth is plated in duplicate and allowed to grow overnight on Mueller-Hinton agar. The MBC is the concentration of the tested compound that kills 99.9% of the microorganisms inoculated into the well.

An example: The lowest concentration with no visible growth from the MIC test is 4 microgram/ml. The contents of the tube having 4 micrograms/ml from the MIC test is plated onto MH agar, in duplicate, and allowed to grow overnight at 35° C. The following day the bacteria are counted to, say, $5 \times 10^2$. The number of bacteria to start with (the inoculum of the MIC tube) is known, say, $5 \times 10^5$. Accordingly, the bacterial population is reduced to $1/1000$ which is the same as having killed 99.9%. Accordingly, in this example the MBC is also 4 microgram/ml and therefore (see below paragraph) the compound is bactericidal.

For the present purposes, a polypeptide of the invention is bactericidal if the MBC value is within a factor of four (two tube dilutions) of the MIC value, preferably within a factor of two (one tube dilution) of the MIC value, more preferably identical to the MIC value.

In particular embodiments, the polypeptide of the invention is bactericidal against at least one of the following bacterial strains: *Bacillus cereus* ATCC 4342, *Enterococcus faecalis* (VRE) ATCC 51299, *Micrococcus luteus* ATCC 9341, and *Staphylococcus aureus* ATCC 29737.

In another particular embodiment, the polypeptide of the invention is not bactericidal against *Enterococcus faecium* ATCC 51559 (see Table 2 in Example 3 herein).

Pharmaceutical Use

In a first aspect, the present invention relates to the antimicrobial polypeptides of the invention for use as medicaments.

Medicaments are used to treat a disease. A disease can be defined as an impairment of health or a condition of abnormal functioning; in other words: A condition of being sick from a particular cause.

The polypeptides of the invention may be used (i) in therapy, i.e., for treatment of a disease, and/or (ii) for prophylaxis, i.e., treatment to prevent the onset of a particular disease ("primary" prophylaxis), and/or the recurrence of symptoms in an existing infection that has been brought under control ("secondary" prophylaxis, maintenance therapy).

The polypeptides of the invention may be used (a) in veterinary medicine, which is the application of medical, diagnostic, and therapeutic principles to companion, domestic, exotic, wildlife, and production animals; and/or (b) in human medicine.

The invention in particular relates to pharmaceutical including veterinary compositions comprising the polypeptide of the invention.

The invention furthermore relates to the use of the polypeptides of the invention in the preparation of a medicament for the treatment of a microbial infection; and to a method of medical treatment comprising administering the polypeptides of the invention to an individual, such as a human being or an animal, in need of medical treatment.

The invention in particular relates to the treatment of a disease caused by microorganisms, e.g., by microbial infections. The treatment with the polypeptides of the invention may serve to control or combat microorganisms as defined above, such as fungi or bacteria, e.g., Gram positive or Gram negative bacteria. The microbial infections may be associated with various diseases, such as lung diseases including, but not limited to, tuberculosis, pneumonia and cystic fibrosis; and sexually transmitted diseases including, but not limited to, gonorrhea and chlamydia. Additional, non-limiting, examples of diseases and microbial infections against which the polypeptide of the invention may be used are mentioned below, as well as in the section headed "Compositions".

In a particular embodiment, the polypeptides of the invention are active against bacteria, preferably against Gram positive bacteria, such as streptococci, enterococci, micrococci, corynebacteria, and bacilli. Examples of Gram positive bacterial strains identified as sensitive to the Lento polypeptide of the invention are: *Bacillus cereus, Corynebacterium jeikeium, Enterococcus faecalis, Enterococcus faecium, Micrococcus luteus*, and *Streptococcus pneumoniae*. In a particular embodiment the *Enterococcus faecium* or *faecalis* strain is VRE (Vancomycin Resistant). In a still further particular embodiment, the *Enterococcus faecium* or faecalis strain is VSE (Vancomycin Sensitive). In addition, certain strains of *Staphylococcus* have been identified as sensitive, viz. *Staphylococcus aureus* ATCC 29213, *Staphylococcus aureus* ATCC 29737, and *Staphylococcus epidermidis* ATCC 12228.

*Bacillus cereus* causes two types of food-borne intoxications, viz. the short-incubation or emetic form of the disease, and the long-incubation or diarrheal form of the disease. Furthermore, *Bacillus cereus* is occasionally implicated in local infections especially involving the eye, causing, e.g., conjunctivitis, keratitis, iridocyclitis, dacryocystitis, orbital abscess, and panophthalmitis.

There are reports documenting that *Corynebacterium jeikeium* can cause a wide variety of infections, including bacterial endocarditis, cavitating or noncavitating pneumonia, CSF shunt infections (CSF designates Cerebro-Spinal Fluid), osteomyelitis, liver abscesses, peritonitis, skin infections, and surgical wound infections.

Clinical diseases and infections caused by *Enterococcus* include urinary tract infections such as urinary bacteremia or septicemia, bacterial endocarditis, diverticulitis, wound infections, intra-abdominal or pelvic infections, skin and soft tissue neonatal infections, meningitis, and otitis.

*Micrococcus luteus* may be associated with infections in the blood (sepsis) and or endocarditis.

Diseases caused by *Streptococcus pneumoniae* include pneumonia, pleuritis, bacteremia, otitis media, meningitis, sinusitis, peritonitis and arthritis.

*Staphylococcus aureus* is a leading cause of skin and soft tissue infections, as well as toxic shock syndrome (TSS) and scalded skin syndrome. It can be distinguished from other species of *Staphylococcus* by a positive result in a coagulase test (all other species are negative). The pathogenic effects of *S. aureus* are mainly associated with the enterotoxin which causes quick onset food poisoning which can lead to cramps and severe vomiting. Another toxin secreted by *S. aureus* is leukocidin, a toxin which destroys white blood cells and leads to the formation of pus and acne. Particularly, *S. aureus* has been found to be the causative agent in such ailments as skin and soft tissue infections, bacteremia, pneumonia, meningitis, boils, arthritis, and osteomyelitis. Of the non-aureus species, *S. epidermis* is the most clinically significant. This bacterium is an opportunistic pathogen which is a normal resident of human skin. Those susceptible to infection by the bacterium are drug users, newborns, elderly, and those using catheters or other artificial appliances.

Accordingly, the polypeptides of the invention may be used for the treatment of any of the diseases listed above.

Use for Cleaning, Disinfection, Preservation, Reduction of Contamination, Etc.

The antimicrobial polypeptides of the invention are typically useful at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, the present invention may also be used in all applications for which known antimicrobial compositions are useful, such as protection of wood, latex, adhesive, glue, paper, cardboard, textile, leather, plastics, and caulking.

Other uses include preservation of foods, beverages, cosmetics such as lotions, creams, gels, ointments, soaps, shampoos, conditioners, antiperspirants, deodorants, mouth wash, contact lens products, enzyme formulations, or food ingredients.

Thus, the antimicrobial polypeptides of the invention may by useful as a disinfectant, e.g., in the treatment of infections in the eye or the mouth, skin infections; in antiperspirants or deodorants; for cleaning and disinfection of contact lenses and teeth (oral care). The polypeptides of the invention may also be used for odor reduction, and/or for reduction of microbes on textile and laundry, which problems have become more pertinent due to the present trend of using lower washing temperatures. An odor evaluation test performed as described in Example 6 herein on various items of very soiled and smelly laundry confirms the potential of the polypeptides of the invention for this particular use.

In general it is contemplated that the antimicrobial polypeptides of the present invention are useful for cleaning, disinfecting or inhibiting microbial growth on any surface. Examples of surfaces, which may advantageously be contacted with the antimicrobial polypeptides of the invention are surfaces of process equipment used, e.g., dairies, chemical or pharmaceutical process plants, water sanitation systems, oil processing plants, paper pulp processing plants, water treatment plants, and cooling towers. The antimicrobial polypeptides of the invention should be used in an amount, which is effective for cleaning, disinfecting or inhibiting microbial growth on the surface in question.

The antimicrobial polypeptides of the invention may additionally be used for cleaning surfaces and cooking utensils in food processing plants and in any area in which food is prepared or served such as hospitals, nursing homes and restaurants. They may also be used as a preservation agent or a disinfection agent in water based paints.

Accordingly, in a second aspect, the invention relates to the use of the antimicrobial polypeptides of the invention (i) for cleaning and/or disinfection of a surface; (ii) for preventing or reducing microbial contamination of an object; and/or (iii) for preservation of a substance.

The invention also relates to methods for killing and/or inhibiting growth of microbial cells comprising contacting the microbial cells with these polypeptides; methods for cleaning and/or disinfection of a surface comprising the step of contacting the surface with these polypeptides; methods for preventing or reducing microbial contamination of an object comprising the step of contacting and/or treating the object with these polypeptides; and methods for preserving a substance comprising the step of contacting the substance with these polypeptides.

Non-limiting examples of surfaces, objects, and substances suitable for being treated (cleaned, disinfected, preserved, etc.) with the polypeptides of the invention are mentioned above.

The following specific food uses of the polypeptides of the invention are contemplated:

Surface treatment of animals in meat industries and in packed meat; treatment of sushi (done today with lysozyme); addition to wine (today lysozyme is used, in substitution of sulphite); treatment of cheese (to substitute nitrite); Sous Vide packaging (heat treatment in vacuum); for hot fills (fastfood etc.); together with MAP/CAP (Modified or Controlled, respectively, Atmospheric Packaging).

Polypeptides, Identity and Hybridization, Fragments and Variants

The polypeptide for use according to the present invention ("the polypeptide of the invention") may be a bacterial or a fungal polypeptide. In a particular embodiment, the polypeptide is a Gram positive bacterial polypeptide such as a *Bacillus* polypeptide or a variant thereof, for example a *Bacillus licheniformis* polypeptide, e.g., derived from *Bacillus licheniformis* ATCC 14580, which is the type strain of *Bacillus licheniformis* and available on request from the American Type Culture Collection, ATCC.

Preferred strains of *Bacillus licheniformis* are positive in the test of Example 4 herein, such as the following strains of *Bacillus licheniformis*: ATCC 14580 (=NCIB 9375), NCIMB 6346 (=DSM 8785), NCTC 1024, NCTC 1025, NCTC 2120, NCTC 7589, NCTC 9932, ATCC 21424, NCIMB 10689, and ATCC 53757.

Specific examples of polypeptides of the invention are: The Lento compound having the amino acid sequence of amino acids 1-85 of SEQ ID NO: 2, as well as the polypeptides having the amino acid sequences of amino acids 1-85 of any one of SEQ ID NOs: 6, 7, and 8.

Additional examples are polypeptides derived from a strain of *Bacillus* which is positive in the test of Example 4 herein. See the section headed "*Bacillus* strains" for further particulars and specific embodiments of such strains.

In a particular embodiment (see Example 5 for details), the polypeptide of the invention has the following denaturation temperatures, as determined by Differential Scanning Calorimetry (DSC): (i) at least 54° C. at pH 2.5, (ii) at least 68° C. at pH 4.0, and/or (iii) at least 59° C. at pH 7.0; preferably (iv) 55° C. at pH 2.5; (v) 69° C. at pH 4.0; and/or (vi) 60° C. at pH 7.0.

In further particular embodiments the polypeptide of the invention has, consists essentially of, or consists of an amino acid sequence which has a degree of identity to amino acids 1-85 of SEQ ID NO: 2 of at least 33%, such as, e.g., the polypeptide of amino acids 1-85 of SEQ ID NO: 2.

The relatedness between two amino acid sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"); e.g., amino acids 1-85 of SEQ ID NO: 2, and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity. In alternative embodiments, the divisor is (i) the length of the longest sequence, or (ii) the length of the overlap of the two sequences.

An exact match occurs when the "invention sequence" and the "foreign sequence" have identical amino acid residues in the same positions of the overlap. The length of a sequence is the number of amino acid residues in the sequence (e.g., the length of amino acids 1-85 of SEQ ID NO: 2 is 85).

In a particular embodiment, the percentage of identity of an amino acid sequence of a polypeptide with, or to, amino acids 1-85 of SEQ ID NO: 2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest, the longest or the overlap of the two amino acid sequences, and iv) converting the result of the division of iii) into percentage.

In the alternative, the degree of identity between two amino acid sequences, as well as the degree of identity between two nucleotide sequences, is determined by the program "align" which is a Needleman-Wunsch alignment (i.e., a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −10 for polypeptides and −16 for nucleotides. The penalties for further residues of a gap are −2 for polypeptides, and −4 for nucleotides. "Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197). See also Myers and Miller, CABIOS (1989) 4:11-17.

In preferred embodiments, the degree of identity to amino acids 1-85 of SEQ ID NO: 2 is at least 35%, or a least 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, 97%, or at least 99%. Polypeptides with any of these degrees of identity to amino acids 1-85 of SEQ ID NO: 2 are referred to as homologous polypeptides. In an alternative embodiment, the degree of identity to amino acids 1-85 of SEQ ID NO: 2 is 32%.

In particular embodiments, the polypeptides of the invention comprise (or have, or consist of) an amino acid sequence that differs by (i) 57, 55, 50, 45, 40, 35, 30, or 25 amino acids from amino acids 1-85 of SEQ ID NO: 2; or by (ii) 20, 19, 18, 17, 16, 15, 14, 13, 12, or 11 amino acids from amino acids 1-85 of SEQ ID NO: 2; or by (iii) 10, 9, 8, 7, 6, or 5 amino acids from amino acids 1-85 of SEQ ID NO: 2. In a further particular embodiment, the polypeptides comprise (or have, or consist of) an amino acid sequence that differs by 4, 3, or 2 amino acids, or by 1 amino acid from amino acids 1-85 of SEQ ID NO: 2.

A fragment of, e.g., amino acids 1-85 of SEQ ID NO: 2 is a polypeptide having one or more amino acids deleted from the amino and/or carboxyl terminus of these amino acid sequences. In one embodiment a fragment contains at least 30, 35, 40, 45, 50, or at least 55 amino acids. In another embodiment a fragment contains at least 65 amino acid residues, or at least 70 amino acid residues, or at least 75 amino acid residues, or at least 80 amino acid residues, or at least 81 amino acid residues, or at least 82 amino acid residues, or at least 83 amino acid residues, or at least 84 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The present invention also relates to the use of polypeptides which are encoded by nucleic acid sequences which hybridize under very low, or low, or medium, or medium-high, or high, or very high stringency conditions with a nucleic acid probe which hybridizes under the same conditions with (i) nucleotides 124-378 of SEQ ID NO: 1, (ii) a subsequence of (i), or (iii) a complementary strand of (i), or (ii) (J. Sambrook, E. F. Fritsch, and T. Maniatis, 1989, Molecular Cloning, A Laboratory Manual, 2nd edition, Cold Spring Harbor, N.Y.). In one particular embodiment the nucleic acid probe is selected from amongst the nucleic acid sequences of (i), (ii), or (iii) above.

The subsequence of nucleotides 124-378 of SEQ ID NO: 1 may be at least 100 nucleotides, or in another embodiment at least 50, 150, or 200 nucleotides.

The nucleic acid sequence of nucleotides 124-378 of SEQ ID NO: 1 or a subsequence thereof, as well as the amino acid sequence of amino acids 1-85 of SEQ ID NO: 2 or a fragment thereof, may be used to design a nucleic acid probe to identify and clone DNA encoding antimicrobial polypeptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labelled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA that hybridizes with the probes described above and which encodes a polypeptide having the desired activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot. For purposes of the present invention, hybridization indicates that the nucleic acid sequence hybridizes to a labelled nucleic acid probe corresponding to the nucleic acid sequence shown in SEQ ID NO: 1, its complementary strand, or a subsequence thereof, under very low to very high stringency conditions. Molecules to which the nucleic acid probe hybridizes under these conditions are detected using X-ray film.

In a particular embodiment, the nucleic acid probe is a nucleic acid sequence which encodes amino acids 1-85 of SEQ ID NO: 2, or subsequences thereof. In another embodiment, the nucleic acid probe is nucleotides 124-378 of SEQ ID NO: 1 (the mature polypeptide coding region of SEQ ID NO: 1).

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes about 15 nucleotides to about 70 nucleotides in length, the carrier material is washed once in 6×SSC plus 0.1% SDS for 15 minutes and twice each for 15 minutes using 6×SSC at 5° C. to 10° C. below the calculated $T_m$.

The present invention also relates to the use of variants of the polypeptide having an amino acid sequence of amino acids 1-85 of SEQ ID NO: 2 comprising a substitution, deletion, and/or insertion of one or more amino acids.

The amino acid sequences of the variant polypeptides may differ from the amino acid sequence of amino acids 1-85 of SEQ ID NO: 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Accordingly, for example, the invention relates to a polypeptide having, or comprising, a sequence as set forth in SEQ ID NO: 2, preferably the mature part thereof, wherein conservative amino acid substitutions comprise replacements, one for another, among the basic amino acids (arginine, lysine and histidine), among the acidic amino acids (glutamic acid and aspartic acid), among the polar amino acids (glutamine and asparagine), among the hydrophobic amino acids (alanine, leucine, isoleucine, and valine), among the aromatic amino acids (phenylalanine, tryptophan and tyrosine), and among the small amino acids (glycine, alanine, serine, threonine and methionine), or any combination thereof, or active fragments thereof.

As defined herein, an "isolated" or "pure" polypeptide is a polypeptide which is essentially free of other polypeptides, e.g., at least 80% pure, preferably at least 85%, 86%, 87%, 88%, 89%, or at least 90% pure, more preferably at least 91%, 92%, 93%, 94%, 95%, or at least 96% pure, as determined by SDS-PAGE (e.g., by coomassie-staining and subsequent scanning by methods known in the art—see Example 2). The SDS-PAGE purity refers to the amount of the polypeptide of the invention, relative to the amount of total protein. In alternative embodiments, the polypeptide may be at least 20%, 40%, 60%, or at least 70% pure.

The amount of total protein can be determined by any method known in the art, e.g., the Kjeldahl method (A.O.A.C., 1984, Official Methods of Analysis 14th ed., Association of Official Analytical Chemists, Washington D.C.), and the amount of the polypeptide of the invention can be determined by SDS-PAGE and subsequent scanning, also by methods known in the art.

Polypeptides for use according to the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

In a specific embodiment, the polypeptide for use according to the invention is a low-allergenic variant, designed to invoke a reduced immunological response when exposed to animals, including man. The term immunological response is to be understood as any reaction by the immune system of an animal exposed to the polypeptide. One type of immunological response is an allergic response leading to increased levels of IgE in the exposed animal. Low-allergenic variants may be prepared using techniques known in the art. For example the polypeptide may be conjugated with polymer moieties shielding portions or epitopes of the polypeptide involved in an immunological response. Conjugation with polymers may involve in vitro chemical coupling of polymer to the polypeptide, e.g., as described in WO 96/17929, WO98/30682, WO98/35026, and/or WO99/00489. Conjugation may in addition or alternatively thereto involve in vivo coupling of polymers to the polypeptide. Such conjugation may be achieved by genetic engineering of the nucleotide sequence encoding the polypeptide. Another way of providing low-allergenic variants is genetic engineering of the nucleotide sequence encoding the polypeptide so as to cause the polypeptides to self-oligomerize, effecting that polypeptide monomers may shield the epitopes of other polypeptide monomers and thereby lowering the antigenicity of the oligomers. Such products and their preparation is described, e.g., in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the polypeptide by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

Recombinant Expression

Suitable expression hosts for the polypeptides of the invention are *Bacillus* host cells, the DNA of which, when harvested and used as a DNA template in a PCR reaction with SEQ ID NOs: 4 and 5 as primers, as described in Example 4, leads to the generation of a PCR fragment of a size of approximately 0.4 kb.

In a particular embodiment, the PCR fragment, when purified and sequenced encodes an amino acid sequence which has at least 33% identity to amino acids 1-85 of SEQ ID NO: 2. In further particular embodiments the PCR fragment, when purified and sequenced, encodes an amino acid sequence which has a degree of identity to amino acids 1-85 of SEQ ID NO: 2 of at least 35%, or a least 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, 97%, or at least 99%.

Suitable host cells are, e.g., the following strains of *Bacillus licheniformis*: ATCC 14580 (=NCIB 9375), NCIMB 6346 (=DSM 8785), NCTC 1024, NCTC 1025, NCTC 2120, NCTC 7589, NCTC 9932, ATCC 21424, NCIMB 10689, and ATCC 53757. A preferred subgroup includes *Bacillus licheniformis* ATCC 14580 (=NCIB 9375), and *Bacillus licheniformis* NCIMB 6346 (=DSM 8785).

Examples of suitable promoters for directing the transcription of the nucleic acid constructs of the present invention in these *Bacillus* host cells are the promoters obtained from *Bacillus licheniformis* alpha-amylase gene (amyL), *Bacillus stearothermophilus* maltogenic amylase gene (amyM), *Bacillus amyloliquefaciens* alpha-amylase gene (amyQ), a CryIIIA promoter (see WO 99/43835), as well as the endogenous Lento promoter of either of the specific *Bacillus licheniformis* host cells mentioned below.

Preferred terminators for the abovementioned *Bacillus* host cells are the terminators from *Bacillus licheniformis* alpha-amylase gene (amyL), and the endogenous Lento terminator from either of these host cells.

A suitable signal peptide coding region is nucleotides 1-123 of SEQ ID NO: 1 which encode amino acids −41 to −1 of SEQ ID NO: 2.

According to the SignalP Version 3.0 software, the predicted signal peptide of SEQ ID NO: 2 is amino acids −41 to −2. This means that the predicted mature protein starts at amino acid −1 of SEQ ID NO: 2, viz. Ala. However, according to Example 2 herein, the N-terminal of the mature protein starts with amino acid +1 of SEQ ID NO: 2, viz. Trp, which means that the signal peptide part spans from amino acids −41 to −1 of SEQ ID NO: 2, which is one amino acid longer than predicted.

Therefore amino acids −1 to +85 of SEQ ID NO: 2 is an alternative mature form of the Lento protein, which is also part of the present invention. Accordingly, any claim and any statement herein referring to amino acids 1-85 of SEQ ID NO: 2 may therefore also, or alternatively, refer to amino acids −1 to +85 of SEQ ID NO: 2. The same is the case for any claim and any statement herein referring to the corresponding part of SEQ ID NO: 1: Nucleotides 121-378 of SEQ ID NO: 1 may be referred to in addition to, or in the alternative to, nucleotides 124-378 of SEQ ID NO: 1.

The SignalP method V. 3.0 is described in Bendtsen et al in Journal of Molecular Biology 2004, 340(4), pp. 783-95. See also Nielsen et al in Proceedings of the Sixth International Conference on Intelligent Systems for Molecular Biology (ISMB 6), AAAI Press, Menlo Park, Calif., pp 122-130, 1998 (V. 2.0); and Nielsen et al in Protein Engineering 10, 1-6 (1997) (V. 1.1).

The resulting polypeptide may be recovered by methods known in the art. For example, the polypeptide may be recovered from the nutrient medium by conventional procedures including, but not limited to, centrifugation, filtration (such as ultrafiltration and/or diafiltration), extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Compositions

Pharmaceutical Compositions

In a third aspect, the present invention relates to an antimicrobial composition comprising a polypeptide of the invention and a suitable carrier. The carrier is preferably pharmaceutically acceptable, and the composition is preferably a pharmaceutical composition.

In addition to, or in the alternative, the composition may comprise a suitable delivery vehicle capable of delivering the antimicrobial polypeptides of the invention to the desired locus when the compositions are used as a medicament.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

The dosage of the polypeptide composition of the invention and other conditions under which the composition is used may be determined on the basis of methods known in the art.

Generally, the composition of the invention comprises an effective amount of the antimicrobial polypeptide of the invention. The term "effective amount" when used herein is intended to mean an amount of the antimicrobial polypeptides of the invention, which is sufficient to inhibit growth of the microorganism in question.

The composition may further comprise another pharmaceutically active agent, such as an additional biocidal agent, such as another antimicrobial polypeptide exhibiting antimicrobial activity as defined above. The biocidal agent may be an antibiotic, as known in the art. Classes of antibiotics include penicillins, e.g., penicillin G, penicillin V, methicillin, oxacillin, carbenicillin, nafcillin, ampicillin, etc.; penicillins in combination with beta-lactamase inhibitors, cephalosporins, e.g., cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g., amphotericin B, nystatin; 5-flucosyn; and azoles, e.g., miconazol, ketoconazol, itraconazol and fluconazol.

In a particular embodiment the biocidal agent is a non-enzymatic chemical agent. In another embodiment the biocidal agent is a non-polypeptide chemical agent.

The invention also relates to wound healing compositions or products such as bandages, medical devices such as, e.g., catheters and further to anti-dandruff hair products, such as shampoos.

Formulations of the antimicrobial polypeptides of the invention may be administered to a host suffering from or predisposed to a microbial infection. Administration may be topical, localized or systemic, depending on the specific microorganism, preferably it will be localized. Generally the dose of the antimicrobial polypeptides of the invention will be sufficient to decrease the microbial population by at least about 50%, usually by at least 1 log, and may be by 2 or more logs of killing. The polypeptides (or compounds) of the present invention may be administered at a dosage that reduces the microbial population while minimizing any side-effects. It is contemplated that the composition will be obtained and used under the guidance of a physician or veterinarian for in vivo use. The antimicrobial polypeptides of the invention may be useful for killing Gram negative bacteria, including *Pseudomonas aeruginosa*, and *Chlamydia trachomatis*; but are particularly useful for killing Gram-positive bacteria, including streptococci such as *Streptococcus pneumonia, S. uberis, S. hyointestinalis, S. pyogenes* or *S. agalactiae*; and staphylococci such as *Staphylococcus aureus, S. epidermidis, S. simulans, S. xylosus*, and *S. carnosus*.

Formulations of the antimicrobial polypeptides of the invention may be administered to a host suffering from or predisposed to a microbial lung infection, such as pneumonia; or to a microbial wound infection, such as a bacterial wound infection.

Formulations of the antimicrobial polypeptides of the invention may also be administered to a host suffering from or predisposed to a skin infection, such as acne, atopic dermatitis or seborrheic dermatitis; preferably the skin infection is a bacterial skin infection, e.g., caused by *Staphylococcus epidermidis, Staphylococcus aureus, Propionibacterium acnes, Pityrosporum ovale* or *Malassezia furfur*.

The antimicrobial polypeptides of the invention are also useful for in vitro formulations to kill microbes, particularly where one does not wish to introduce quantities of conventional antibiotics. For example, the antimicrobial polypeptides of the invention may be included as an additive for in vitro cultures of cells, to prevent the overgrowth of microbes in tissue culture.

The susceptibility of a particular microbe to killing with the antimicrobial polypeptides of the invention may be determined by in vitro testing, as detailed in the experimental section. Typically a culture of the microbe is combined with the antimicrobial polypeptide at varying concentrations for a period of time sufficient to allow the protein to act, usually between about one hour and one day. The viable microbes are then counted, and the level of killing determined.

Microbes of potential interest include, but are not limited to, Gram-negative bacteria, for example: *Citrobacter* sp.; *Enterobacter* sp.; *Escherichia* sp., e.g., *E. coli*; *Klebsiella* sp.; *Morganella* sp.; *Proteus* sp.; *Providencia* sp.; *Salmonella* sp., e.g., *S. typhi, S. typhimurium*; *Serratia* sp.; *Shigella* sp.; *Pseudomonas* sp., e.g., *P. aeruginosa*; *Yersinia* sp., e.g., *Y. pestis, Y. pseudotuberculosis, Y. enterocolitica*; *Franciscella* sp.; *Pasturella* sp.; *Vibrio* sp., e.g., *V. cholerae, V. parahemolyticus*; *Campylobacter* sp., e.g., *C. jejuni*; *Haemophilus* sp., e.g., *H. influenzae, H. ducreyi*; *Bordetella* sp., e.g., *B. pertussis, B. bronchiseptica, B. parapertussis*; *Brucella* sp., *Neisseria* sp., e.g., *N. gonorrhoeae, N. meningitidis*, etc. Other bacteria of interest include *Legionella* sp., e.g., *L. pneumophila*; *Listeria* sp., e.g., *L. monocytogenes*; *Mycoplasma* sp., e.g., *M. hominis, M. pneumoniae*; *Mycobacterium* sp., e.g., *M. tuberculosis, M. leprae*; *Treponema* sp., e.g., *T. pallidum*; *Borrelia* sp., e.g., *B. burgdorferi*; *Leptospirae* sp.; *Rickettsia* sp., e.g., *R. rickettsii, R. typhi*; *Chlamydia* sp., e.g., *C. trachomatis, C. pneumoniae, C. psittaci*; *Helicobacter* sp., e.g., *H. pylori*, etc.

Non-bacterial pathogens of potential interest include fungal and protozoan pathogens, e.g., *Plasmodia* sp., e.g., *P. falciparum*, *Trypanosoma* sp., e.g., *T. brucei*; shistosomes; *Entaemoeba* sp., *Cryptococcus* sp., *Candida* sp., e.g., *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semiweekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The antimicrobial polypeptides of the invention may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention may be administered alone, in combination with each other, or they may be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds may be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds may be formulated into preparations for injections by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds may be utilized in aerosol formulation to be administered via inhalation. The compounds of the present invention may be formulated into pressurized acceptable propellants such as dichlorodifluoromethane, propane, nitrogen and the like.

The compounds may be used as lotions, for example to prevent infection of burns, by formulation with conventional additives such as solubilizers, isotonic agents, suspending agents, emulsifying agents, stabilizers and preservatives.

Furthermore, the compounds may be made into suppositories by mixing with a variety of bases such as emulsifying bases or water-soluble bases. The compounds of the present invention may be administered rectally via a suppository. The suppository may include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will normally be neutral or acidic lipids, such as cholesterol, phosphatidyl serine, phosphatidyl glycerol, and the like.

For preparing the liposomes, the procedure described by Kato et al. (1991) J. Biol. Chem. 266:3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

The antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g., penicillin G, penicillin V, methicillin, oxacillin, carbenicillin, nafcillin, ampicillin, etc.; penicillins in combination with beta-lactamase inhibitors, cephalosporins, e.g., cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents may also be useful, including polyenes, e.g., amphotericin B, nystatin; 5-flucosyn; and azoles, e.g., miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g., interferon gamma, tumor necrosis factor alpha, interleukin 12, etc.

Detergent Compositions

The antimicrobial polypeptides of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptides of the invention. The detergent additive as well as the detergent composition may comprise one or more enzymes as is known in the art of detergent additives (detergent enzymes), such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the polypeptides of the invention, and the additional enzyme(s), if any, should be compatible with the selected detergent, (i.e., pH-optimum, compatibility with other enzymatic and non-enzymatic ingredients, etc.), and the enzyme(s) should be present in effective amounts.

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583. Further examples of useful proteases are the variants described in WO 92/19729, WO 98/20115, WO 98/20116, and WO 98/34946. Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258068 and EP 305216 or from *H. insolens* as described in WO 96/13580, a *Pseudomonas* lipase, e.g., from *P. alcaligenes* or *P. pseudoalcaligenes* (EP 218272), *P. cepacia* (EP 331376), *P. stutzeri* (GB 1372034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Suitable amylases (alpha- and/or beta-) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1296839. Examples of useful amylases are the variants described in WO 94/02597, WO 94/18314, WO 96/23873, and WO 97/43424. Commercially available amylases are Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care benefits. Examples of such cellulases are cellulases described in EP 495257, EP 531372, WO 96/11262, WO 96/29397, and WO 98/08940. Other examples are cellulase variants such as those described in WO 94/07998, EP 531315, U.S. Pat. No. 5,457,046, U.S. Pat. No. 5,686,593, U.S. Pat. No. 5,763,254, WO 95/24471, WO 98/12307 and WO 1999/001544.

Commercially available cellulases include Celluzyme™, and Carezyme™ (Novozymes A/S), Clazinase™, and Puradax HA™ (Genencor International Inc.), and KAC-500 (B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

The antimicrobial polypeptides of the invention, and, optionally, the detergent enzyme(s) may be included in a detergent composition by adding separate additives containing the antimicrobial polypeptides of the invention, potentially also one or more enzymes, or by adding a combined additive comprising the antimicrobial polypeptide, and possibly enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. No. 4,106,991 and 4661452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The antimicrobial polypeptide(s), as well as the optional enzyme(s) of the detergent composition of the invention, may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any polypeptide, i.e., in particular the antimicrobial polypeptide of the invention, and optionally the enzyme(s), may be added in an amount corresponding to 0.01-100 mg of enzyme protein per liter of wash liquor, preferably 0.01-90, 0.01-80, 0.01-70, 0.01-60, 0.01-50, 0.01-40, 0.01-30, 0.01-20, 0.01-10, or 0.01-5 mg of enzyme protein per liter of wash liquor, more preferably an amount corresponding to 0.05-20, 0.05-15, 0.05-10, or 0.05-5 mg of enzyme protein per liter of wash liquor, most preferably in an amount corresponding to 0.1-10, 0.1-8, 0.1-6, 0.1-5, 0.1-4, 0.1-3, 0.1-2, or 0.1-1 mg of enzyme protein per liter of wash liquor.

The enzyme of the invention may additionally be incorporated in the detergent formulations disclosed in WO 97/07202.

*Bacillus* Strains

In a fourth aspect, the invention relates to the pharmaceutical use, as well as all other uses referred to above, of a strain of *Bacillus* which is positive in the test of Example 4 herein.

Accordingly, each and every particular embodiment of the first, second, and third aspect of the present invention are specifically applicable also to this aspect of the invention, and specifically included herein, e.g.:

I. Use of a *Bacillus* strain which is positive in the test of Example 4 herein as an antimicrobial agent.

II. A *Bacillus* strain which is positive in the test of Example 4 herein for use as a medicament.

III. A *Bacillus* strain which is positive in the test of Example 4 herein for use as a veterinary or human medicament.

IV. The *Bacillus* strain which is positive in the test of Example 4 herein according to any one of II or III for use in therapy or prophylaxis.

V. Use of a *Bacillus* strain which is positive in the test of Example 4 herein in the preparation of a medicament for the treatment of a microbial infection.

VI. The use according to V, wherein the medicament is for veterinary or human use.

VII. The use according to any one of V or VI for therapy or prophylaxis.

IIX. The use according to I (i) for cleaning and/or disinfection of a surface; (ii) for preventing or reducing microbial contamination of an object; and/or (iii) for preservation of a substance.

IX. A method for killing and/or inhibiting growth of microbial cells comprising contacting the microbial cells with a *Bacillus* strain which is positive in the test of Example 4 herein.

X. A method of medical treatment comprising administering a *Bacillus* strain which is positive in the test of Example 4 herein to an individual in need of medical treatment.

XI. The method according to X, wherein the individual is an animal or a human being.

XII. The method according to any one of X or XI for therapy or prophylaxis.

XIII. The method according to any one of X to XII for treatment of a disease caused by microorganisms.

XIV. A method for cleaning and/or disinfection of a surface comprising the step of contacting the surface with a *Bacillus* strain which is positive in the test of Example 4 herein.

XV. A method for preventing or reducing microbial contamination of an object comprising the step of contacting and/or treating the object with a *Bacillus* strain which is positive in the test of Example 4 herein.

XVI. A method for preserving a substance comprising the step of contacting the substance with *Bacillus* strain which is positive in the test of Example 4 herein.

XVII. An antimicrobial composition comprising a *Bacillus* strain which is positive in the test of Example 4 herein and a suitable carrier.

IIXX. The antimicrobial composition according to XVII wherein the carrier is pharmaceutically acceptable.

The expression "a strain of *Bacillus* which is positive in the test of Example 4 herein" means that the DNA of the *Bacillus* strain, when harvested and used as a DNA template in a PCR reaction with SEQ ID NOs: 4 and 5 as primers, leads to the generation of a PCR fragment of a size of approximately 0.4 kb. This test serves to identify strains with a Lento-like gene.

In a particular embodiment, the *Bacillus* strain is used in the form of spores. Spores may be exospores or, preferably, endospores. An endospore is any spore that is produced within an organism (usually a bacterium).

In another particular embodiment, the PCR fragment, when purified and sequenced encodes an amino acid sequence which has at least 33% identity to amino acids 1-85 of SEQ ID NO: 2. In further particular embodiments the PCR fragment, when purified and sequenced, encodes an amino acid sequence which has a degree of identity to amino acids 1-85 of SEQ ID NO: 2 of at least 35%, or a least 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, 97%, or at least 99%.

In further particular embodiments, the strain of *Bacillus* is a strain of *Bacillus licheniformis*, preferably selected from the following strains of *Bacillus licheniformis*: ATCC 14580 (=NCIB 9375), NCIMB 6346 (=DSM 8785), NCTC 1024, NCTC 1025, NCTC 2120, NCTC 7589, NCTC 9932, ATCC 21424, NCIMB 10689, and ATCC 53757. A preferred subgroup includes *Bacillus licheniformis* ATCC 14580 (=NCIB 9375), and *Bacillus licheniformis* NCIMB 6346 (=DSM 8785).

For a taxonomical classification and identification of bacteria reference is had to Bergey's Manual of Systematic Bacteriology (1986), Vol. 2, ISBN0-683-0783; see for example p 1104 section 13, Endospore forming Gram positive rods and cocci; p. 1105 Genus *Bacillus*; pp. 1105-1129 description of the genus; pp. 1130-1138 description of the individual *Bacillus* species, e.g., on p. 1132 *Bacillus licheniformis*). In the alternative, the well-known 16SrRNA sequence analysis can be used (see, e.g., Johansen et al., Int. J. Syst. Bacteriol, 1999, 49, 1231-1240, in particular the Methods section on p. 1233, $2^{nd}$ column); or taxonomy experts can be consulted, e.g., from DSMZ or other recognized depositary institutes.

Strains of *Bacillus*, such as strains of *Bacillus licheniformis*, are known in the art and available from, e.g., culture collections like ATTC mentioned above, or they can be isolated from nature. Preparations of live, or livable, *Bacillus* cells may be prepared as is known in the art. Examples of such cells are vegetative cells, and spores such as endospores. In one embodiment a fermentation extract of the *Bacillus* strain is used, for example in the form of a spray dried fermentation liquor.

The test of Example 4 is a PCR reaction, in this example conducted with DNA isolated from various strains of *Bacillus licheniformis*. In a particular embodiment of this test, the DNA used as template for the PCR reaction is chromosomal DNA which can be isolated by methods known in the art. The result of the Example 4 test is positive when a PCR fragment of the right size is obtained. In example 4, the right size is indicated as 0.4 kb. In a particular embodiment, the right size is between 0.35 kb and 0.44 kb (=350 bp-440 bp). In alternative embodiments, the right size is 330-430 bp, 340-420 bp, 350-410 bp, 360-400 bp, 370-390 bp, or 385-395 bp. The size of the coding sequence (CDS) of SEQ ID NO: 1 is approximately 380 bp (viz. 378 bp).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Example 1

Preparation of the Lento Compound

The Lento compound was prepared by purification of a *Bacillus licheniformis* ATCC 14580 fed-batch fermentation broth as described below.

Fermentation

All media were sterilized by methods known in the art. Unless otherwise described, tap water was used. The ingredient concentrations referred to in the below recipes are before any inoculation.

Media:

LB agar: 10 g/l peptone from casein (such as, Fluka catalogue no. 95039, tryptic digest from casein); 5 g/l yeast extract (manufactured by autolysis of *Saccharomyces cerevisiae*, e.g., catalogue no. 9512 from Organotechnie S.A., 27, avenue Jean Mermoz, F-93120 La Courneuve, France); 10 g/l sodium chloride; 12 g/l Bacto-agar (LB-agar (Miller), Merck catalogue no. 110283) adjusted to pH 7.0+/−0.2.

M-9 buffer: Di-Sodiumhydrogenphosphate, $2H_2O$ 8.8 g/l; potassiumdihydrogenphosphate 3 g/l; sodium chloride 4 g/l; magnesium sulphate, $7H_2O$ 0.2 g/l (deionized water is used in this buffer).

PRK-50: 110 g/l soy grits; Di-sodiumhydrogenphosphate, $2H_2O$ 5 g/l; antifoam (such as, e.g., Struktol SB2121, Schill & Seilacher, Hamburg, Germany) 1 ml/l; pH adjusted to 8.0 with $NaOH/H_3PO_4$ before sterilization.

Make-up medium: Tryptone (Casein hydrolysate such as, e.g., Bacto™ Tryptone pancreatic digest of casein catalogue no. 211699) 30 g/l; magnesium sulphate, $7H_2O$ 4 g/l; di-potassiumhydrogenphosphate 7 g/l; di-sodiumhydrogenphosphate, $2H_2O$ 7 g/l; di-ammoniumsulphate 4 g/l; citric acid 0.78 g/l; vitamins (thiamin-dichlorid 34.2 mg/l; riboflavin 2.9 mg/l; nicotinic acid 23 mg/l; calcium D-pantothenate 28.5 mg/l; pyridoxal-HCl 5.7 mg/l; D-biotin 1.1 mg/l; folic acid 2.9 mg/l); trace metals ($MnSO_4$, $H_2O$ 39.2 mg/l; $FeSO_4$, $7H_2O$ 157 mg/l; $CuSO_4$, $5H_2O$ 15.6 mg/l; $ZnCl_2$ 15.6 mg/l); Antifoam (Struktol SB2121, see above) 1.25 ml/l; pH adjusted to 6.0 with $NaOH/H_3PO_4$ before sterilization. Monopropylene glycol (MPG) 24 ml/l was added 28 and 47 hours after inoculation (i.e., after approximately 1 and 2 days, respectively), in total 48 ml/l of MPG was added.

Feed-medium: Glucose, $1H_2O$ 820 g/l

Procedure:

*Bacillus licheniformis* ATCC 14580 was grown on LB agar slants for one day at 37° C. The agar was then washed with M-9 buffer, and the optical density (OD) at 650 nm of the resulting cell suspension was measured. Inoculum shake flasks (with 100 ml medium PRK-50) were inoculated with an inoculum of OD (650 nm)×ml cell suspension=0.1 (which means that the required amount of inoculum in ml is found by dividing 0.1 by the OD (650 nm) of the inoculum cell suspension). The shake flasks were incubated at 37° C. at 300 rpm for 20 hr.

The fermentors used were standard lab fermentors equipped with a temperature control system, pH control with ammonia water and phosphoric acid, dissolved oxygen electrode to measure >20% oxygen saturation through the entire fermentation.

The fermentation in the main fermentor (fermentation tank) was started by inoculating the main fermentor with the growing culture from an inoculum shake flask. The inoculated volume was 10% of the make-up medium (80 ml for 720 ml make-up medium, resulting in 800 ml initial broth after inoculation).

The fermentation parameters were: Temperature 41° C.; pH between 6.8 and 7.2 (using ammonia water and phosphoric acid, control 6.8 (ammonia water), 7.2 phosphoric acid). Aeration 1.5 liter/min/kg of the fermentation broth weight, agitation: 1500 rpm.

Feed-medium was added as follows: Initial feed rate 0.05 g/min/kg at the start of the fermentation, increasing linearly to 0.16 g/min/kg after 8 hours, and remaining at 0.16 g/min/kg until the end of the fermentation (by reference to the starting weight of the fermentation broth, just after the inoculation).

After 3 days (70 hours) the fermentation broth was harvested and purified as described below.

Purification

The fermentation broth was centrifuged (20000×g, 20 min) and the supernatants were carefully decanted from the precipitates. The combined supernatants were filtered through a Seitz K-250 plate and then through a Seitz EKS plate in order to remove the rest of the *Bacillus* host cells. The conductivity of the EKS filtrate was 10 mS/cm. 100 ml EKS filtrate was diluted 10× in 20 mM $CH_3COOH$, 50 mM $H_3BO_3$, 1 mM $CaCl_2$, adjusted to pH 4.5 with NaOH and pH of the diluted EKS filtrate was adjusted to pH 4.5 with 20% $CH_3COOH$. The diluted EKS filtrate was applied to a 19 ml SP-sepharose FF column equilibrated in 20 mM $CH_3COOH$, 50 mM $H_3BO_3$, 1 mM $CaCl_2$, adjusted to pH 4.5 with NaOH. After washing the column extensively with the equilibration buffer, the Lento protein was eluted with a linear NaCl gradient (0->0.5M) in the same buffer. Fractions containing the Lento protein were identified by SDS-PAGE analysis and pooled and diluted 10 times with demineralized water to reduce the conductivity of the pool. The pool was applied to an 8 ml SOURCE S column equilibrated in the same equilibration buffer (20 mM $CH_3COOH$, 50 mM $H_3BO_3$, 1 mM $CaCl_2$, adjusted to pH 4.5 with NaOH) and after washing the column extensively with the equilibration buffer, the Lento protein was eluted with a linear NaCl gradient (0->1.0 M) in the same buffer. Fractions from the column were analysed by SDS-PAGE analysis and fractions containing the Lento protein were pooled and applied to a 120 ml Superdex 75 size-exclusion column equilibrated in 20 mM $CH_3COOH$, 50 mM $H_3BO_3$, 100 mM NaCl, 1 mM $CaCl_2$, adjusted to pH 4.5 with NaOH. The Superdex 75 column was eluted with the same buffer and fractions from the column were analysed by SDS-PAGE analysis. Fractions giving rise to a strong band at 12 kDa on the coomassie stained SDS-PAGE gel were pooled as the purified Lento protein preparation. The preparation was at least 90% pure judged from a coomassie stained SDS-PAGE gel, and the relative molecular weight as determined by SDS-PAGE was Mr=12 kDa. The N-terminal sequence was:

WNVPGYHYQY. (SEQ ID NO: 3)

Example 2

Determination of Concentration

A Lento protein preparation with a purity of above 96% was prepared as described in Example 1, and glycerol was added to 50% (w/w) final concentration. The purity was above 96%, as measured by HPLC (using a Waters 2690 separation module and a Waters 2487 UV detector, detecting at 280 nm, using columns ACE C18 5 micro-m 100 Å 150×3.0 mm and Waters µ-Bondapak C18 20×3.9 mm (guard column), a flow rate of 0.5 ml/min, an injection volume of 10 microliters, mobile phase A: $H_2O$ 18 MΩ+0.1% TFA (Tri-Fluor Acetic acid), mobile phase B Acetonitrile+0.1% TFA). The glycerol formulated Lento protein was stored cold in a refrigerator. This preparation was used as Lento protein standard. The concentration of the standard was 3.6 mg pure protein/ml by, as determined by Amino Acid Analysis (as described below).

The purity and concentration of various other Lento samples were determined by an SDS-PAGE gel method as also described below, by reference to this standard.

Amino Acid Analysis (AAA)—Concentration of Lento Protein Standard

The peptide bonds of the Lento protein standard sample were subjected to acid hydrolysis, followed by separation and quantification of the released amino acids on a Biochrom 20 Plus Amino Acid Analyser, commercially available from Bie & Berntsen A/S, Sandbaekvej 5-7, DK-2610 Roedovre, Denmark, according to the manufacturer's instructions. For the acid hydrolysis, the protein sample was dried in a vacuum centrifuge, resolved in 18.5% (vol/vol) HCl+0.1% (vol/vol) phenol and incubated for 16 hr at 110° C. After incubation, the sample was again dried in the vacuum centrifuge, resolved in loading buffer (0.2 M Na-Citrate, pH 2.2) and loaded onto the Biochrom 20 Plus Amino Acid Analyser.

For the quantification, the hydrolysed sample was loaded onto a column of the cation-exchange resin UltroPac no. 8, Sodium-form, which is commercially available from Bie & Berntsen A/S, catalogue no. 80-2104-15. Buffers of varying pH (pH 1 to pH 8) and ionic strength were pumped through the column according to the manufacturer's instructions referred to above, to separate the various amino acids. The column temperature was accurately controlled, also according to the manufacturer's instructions (from 53° C. to 92° C. and back to 53° C.) in order to ensure the required separation. The column eluent was mixed with ninhydrin reagent (Bie & Berntsen, catalogue no. 80-2038-07) and the mixture passed through the high temperature reaction coil of the Amino Acid Analyser. In the reaction coil, ninhydrin reacted with the amino acids to form coloured compounds, the amount of which was directly proportional to the quantity of amino acid present.

Concentration of Lento Protein Samples

SDS-PAGE purity and concentration of various Lento samples were determined by the following procedure (all Novex products referred to are commercially available from Invitrogen, see www.invitrogen.com):

50 microliter Lento solution (0.1-1.0 mg Lento per ml) was mixed with 5 microliter 1% (w/v) EDTA+10 microliter 6% PMSF+10 microliter 0.5M DTT+25 microliter NuPage LDS sample buffer (NP0007 from NOVEX) in an Eppendorf tube, and the tube was heated to 95° C. for 5 minutes. 10 microliter sample was applied to a 10% Tris-Bis precast gel (NP0301BOX from NOVEX). The electrophoresis was performed with a MES running buffer (MES=2-(N-morpholino) ethan sulfonic acid; NP0002 from NOVEX)+antioxidant (NP0005 from NOVEX) at a 200V constant voltage according to the manufacturer's instructions. After electrophoresis, the gel was gently shaken in 10% acetic acid+50% EtOH for 10 minutes. The gel was then gently shaken with Colloidal Blue staining solution (46-7016 from NOVEX) for minimum three hours and washed by gentle shaking for 2 to 4 hours with distilled water with several changes of distilled water. The wet gel was scanned with a BioRad Calibrated Densitometer GS-800 equipped with Quantity One software (version 4.6.0, BioRad) and the Lento protein was quantified according to the manufacturer's instructions. The Lento-standard described above was used as a standard, viz. in three-four dilutions within the range of 0.1-1.0 mg/ml.

Example 3

Antimicrobial Activity

A Lento preparation with a purity of at least 96% (prepared as described in Example 1) was used to test a number of publicly available bacterial strains obtained from the American Type Culture Collection (ATCC, 1549 Manassas, Va. 20108, US). Ciprofloxacin and vancomycin were included as controls and were purchased from USP (Rockville, Md.), dissolved in double distilled $H_2O$ and diluted in Mueller-Hinton Broth (MHB) (Difco Catalog number 275730, Becton Dickinson and Company, Sparks, Md., US; 2.0 g beef extract powder, 17.5 g acid digest of casein, 1.5 g starch—per 1000 ml water). Serial two fold dilutions were made of each antibiotic tested from 128 microgram/ml to 0.125 microgram/ml in MHB, and plated to a 96-well plate.

Minimal inhibitory concentrations (MIC) and minimal bactericidal concentrations (MBC) were determined by broth microdilution in MHB as described by the NCCLS (National Committee for Clinical Laboratory Standards, in: Methods for Determining Bactericidal Activity of Antimicrobial Agents; Approved Guideline. National Committee for Clinical Laboratory Standards (M26-A), Vol. 19, 1999).

Briefly, the MIC was determined by microbroth dilution assay in a 96 well plate. 4-5 colonies of each bacterium tested were added to 5 ml of MHB, placed in a 35° C. shaker until the OD 600 nm reached 0.08-0.10. The inoculum was diluted 1:100 and 50 microliters were added to each well which contained 50 microliters of serial two fold dilutions of Lento, vancomycin or ciprofloxacin. Each concentration of antibiotic or Lento was tested in duplicate. The plate was placed at 35° C. overnight. MICs were determined after 24 hour incubation and defined by the well containing the lowest amount of antibiotic with no visible growth.

Some of the bacteria tested were resistant to antibiotics, and the following abbreviations were used to indicate such resistance: VRE denotes Vancomycin-Resistant *Enterococcus*, MRSA Methicillin Resistant *Staphylococcus aureus*, GISA Glycopeptide Intermediate-Resistant *Staphylococcus aureus*, PSRSP Penicillin and trimethoprim-Sulfamethoxazole Resistant *Streptococcus pneumoniae*, and TCRSP Tetracycline and Chloramphenicol Resistant *Streptococcus pneumoniae*.

TABLE 1

MIC results

| Gram | Strains | ATCC | Lento | Ciprofloxacin | Vancomycin |
|---|---|---|---|---|---|
| − | *Acinetobacter* sp. | 49137 | >256 | 0.0625 | >64 |
| − | *Burkholderia cepacia* | 25416 | >256 | 0.25 | >64 |
| − | *Eschericia coli* | 10536 | >256 | 0.0625 | >64 |
| − | *Eschericia coli* | 25922 | >256 | 0.0625 | >64 |
| − | *Eschericia coli* | 35218 | >256 | 0.0625 | >64 |
| − | *Klebsiella pneumoniae* | 10031 | >256 | 0.0625 | >64 |
| − | *Pseudomonas aeruginosa* | 27853 | >256 | 0.125-0.25 | >64 |
| − | *Salmonella typhimurium* | 13311 | >256 | 0.0625 | >64 |
| − | *Shigella dysenteriae* | 11835 | >256 | 0.0625 | >64 |
| − | *Stenotrophomas maltophilia* | 13637 | >256 | 0.125 | 32 |
| + | *Bacillus cereus* | 4342 | 0.5-1 | 0.125 | 1 |
| + | *Corynebacterium jeikeium* | 43216 | 0.125 | 0.125 | 0.25 |
| + | *Corynebacterium jeikeium* | 43734 | 2 | 0.0625 | 0.25 |
| + | *Enterococcus faecalis* (VRE) | 51299 | 8 | 0.5 | 2 |
| + | *Enterococcus faecium* | 51559 | 4 | >64 | |
| + | *Micrococcus luteus* | 9341 | 8 | 1 | 0.5 |
| + | *Staphylococcus aureus* (MRSA) | 33591 | >256 | 0.125 | 1 |
| + | *Staphylococcus aureus* subsp. *aureus* (MRSA & GISA) | 700789 | >256 | 16 | 2 |
| + | *Staphylococcus aureus* subsp. *aureus* (MRSA) | 700788 | >256 | 8 | 2 |
| + | *Staphylococcus aureus* | 29213 | 64 | 0.125 | 0.5 |
| + | *Staphylococcus aureus* | 29737 | 8-32 | 0.0625-0.25 | 0.5 |
| + | *Staphylococcus aureus* | 27734 | >256 | 8 | 1 |
| + | *Staphylococcus aureus* (GISA) | 700699 | >256 | 16 | 8 |
| + | *Staphylococus aureus* (GISA) | 700787 | >256 | 16 | 8 |
| + | *Staphylococcus epidermidis* | 12228 | 128 | 0.0625 | 1 |
| + | *Streptococcus pneumoniae* | 49619 | 1-2 | 0.5 | 0.5-1 |
| + | *Streptococcus pneumoniae* (PSRSP) | 700671 | 2 | 1-2 | 0.5 |
| + | *Streptococcus pneumoniae* | 700676 | 4 | 1 | 0.25 |
| + | *Streptococcus pneumoniae* (TCRSP) | 700902 | 4-8 | 0.5-1 | 0.25 |

To determine the MBC, 10 microliter from each well with no growth was plated in duplicate and allowed to grow overnight on Mueller-Hinton agar (Difco Catalog number 225250, Becton Dickinson and Company, Sparks, Md., US; 2.0 g beef extract powder, 17.5 g acid digest of casein, 1.5 g starch, 17 g agar—per 1000 ml of water). The MBC is based on the inoculum concentration, which was determined by plating in duplicate 50 microliter of $10^{-2}$, $10^{-3}$, and $10^{-4}$ of the inoculum used for MICs. MBCs were determined as described by the NCCLS guidelines (cited above). The MBC is the concentration of the tested compound that kills 99.9% of the microorganism inoculated into the well.

The MIC results are shown in Table 1 below, and the MBC results in Table 2 below.

Due to the two fold serial dilution principle of the MIC assay, the inaccuracy in the determination of the MIC value may be up to four-fold, or even higher. Of course, more accurate determinations can be made by performing serial dilutions of various starting concentrations of the polypeptide. The inaccuracy in the determination of the MBC values is as described above for the MIC values.

From the above results it appears that the Lento compound has: 1) A pronounced antimicrobial effect on a number of Gram-positive bacterial strains (with the exception of certain strains of *Staphylococcus*); and 2) an uncertain if any antimicrobial effect on Gram-negative bacterial strains.

For the Gram-positive bacterial strains tested, the MIC values were in the range of from 0.1 to 128 microgram/ml.

TABLE 2

MBC results

| Gram | Strains | ATCC | MIC | MBC |
|---|---|---|---|---|
| + | *Bacillus cereus* | 4342 | 1 | 1 |
| + | *Enterococcus faecalis* (VRE) | 51299 | 64 | 64 |
| + | *Enterococcus faecium* | 51559 | 4 | >64 |
| + | *Micrococcus luteus* | 9341 | 8 | 8 |
| + | *Staphylococcus aureus* | 29737 | 32 | 32 |

For drugs considered "bactericidal", the MBC value is within two tube dilutions, viz. four fold, of the MIC value, meaning, the organisms were not simply inhibited, but rather, were killed. Based on this definition, Lento is bactericidal against all bacteria tested with the exception of *E. faecium* ATCC 51559.

Example 4

*Bacillus* Strains with Lento-Like Genes, as Identified by PCR

Genes similar to the gene encoding the Lento protein (SEQ ID NO: 1) were identified in a number of other *Bacillus licheniformis* strains by PCR. DNA for use as a template for the PCR reaction was isolated from eleven different *Bacillus licheniformis* strains grown overnight at 37° C. on TY agar plates (for recipe, see Example 1). One inoculation tube with cells from each strain were suspended in 0.1 ml $H_2O$ and boiled for 10 min, centrifuged, and 5 microliters supernatant from each was used as DNA template in PCR reactions as described below.

The PCR reactions were run in "Pure Taq™ Ready-To_Go™ PCR Beads" from Amersham Biosciences: 5 microliters DNA template+2×1 microliter of primer Pep481 (SEQ ID NO: 4) and Pep482 (SEQ ID NO: 5)+18 microliters $H_2O$.

PCR program: 1) 95° C. 3 min; 2) 95° C. 10 sec; 3) 65° C. 30 sec—1° C. pr. cycle; 4) 72° C. 1 min; 5) Go To 2) 9 times; 6) 95° C. 10 sec; 7) 55° C. 30 sec; 8) 72° C. 1 min; 9) Go To 6) 19 times; 10) 72° C. 5 min; 11) 4° C. forever, which means that following step 10) the temperature is lowered to 4° C.

```
Primers:
                                          (SEQ ID NO: 4)
Pep481 AATTACGCGTGTTGGTGCGATAGTAGTAACG-3'

(SEQ ID NO: 5)
Pep482 TTAAGAATTCGAATGAAAGAGGAGGAATG-3'
```

The resulting 0.4 kb PCR fragment from five positive strains (positive meaning giving DNA band of the right size) were purified and used in a DNA sequencing experiment, using once again as sequence primers the Pep481 (SEQ ID NO: 4) and Pep482 (SEQ ID NO: 5) primers.

Three of the five positive strains gave the same DNA sequence: *Bacillus licheniformis* ATCC 14580, *Bacillus licheniformis* NCIMB 6346 (=DSM 8785) and *Bacillus licheniformis* strain 712, resulting in the amino acid sequence of SEQ ID NO: 2. In *Bacillus licheniformis* strain 470 DNA changes resulted in two amino acid changes (SEQ ID NO: 7), however none in the mature peptide. In *Bacillus licheniformis* strain 009 DNA changes resulted in fifteen amino acid changes (SEQ ID NO: 6), eight of which are in the mature peptide. Furthermore, a consensus sequence (SEQ ID NO: 8) was derived from SEQ ID NOs: 2, 6, and 7.

Note that, in this experiment, the nucleotides encoding the seven C-terminal amino acids of SEQ ID NO: 2 are included in the Pep481 primer (SEQ ID NO: 4), and the seven C-terminal amino acid residues of SEQ ID NOs: 6-7 may therefore not be correct. However the correctness of SEQ ID NOs: 6-7 was later confirmed.

In addition, 44 other strains of *Bacillus licheniformis* were tested as described above. A positive PCR-response was found in 27 of these strains. Examples of additional publicly available strains of *Bacillus licheniformis* found to be Lento-positive have the following deposit numbers: NCTC 1024, NCTC 1025, NCTC 2120, NCTC 7589, NCTC 9932, ATCC 21424, NCIMB 10689, ATCC 53757. NCTC is the National Collection of Type Cultures. ATCC is the American Type Culture Collection. NCIMB is the National Collection of Industrial, Marine and Food Bacteria.

Example 5

Thermostability

Differential Scanning Calorimetry (DSC) was used to determine temperature stability of the Lento protein at pH 2.5, 4.0 and 7.0. Purified Lento in a concentration of about 2 mg/ml was dialysed over night at 4° C. against appropriate buffer and run on a VP-DSC instrument (MicroCal) with a constant scan rate of 1.5° C./min from 20 to 90° C. Data-handling was performed using the MicroCal Origin software (version 4.10), and denaturation temperature was defined as temperature at the apex of the enthalpy peak. In 10 mM citric acid, 50 mM sodium chloride, pH 2.5, Lento was found to have a denaturation temperature of 55° C. In 10 mM sodium acetate, 50 mM NaCl, pH 4.0, Lento denatured at 69° C., and in 10 mM sodium phosphate, 50 mM NaCl, pH 7.0 the denaturation temperature was 60° C.

Example 6

Use in Detergents

The Lento polypeptide was produced in a pilot scale fermentor. The culture broth was pre-treated and the cells removed. Coarse filtration and germ filtration steps were followed by UF-concentration and a further filtration step. The sample was subsequently freeze-dried and the amount of the Lento polypeptide quantified by comparison to a standard material as described in Example 2.

Really soiled, smelly laundry from Warwick Equest Limited (Greencroft Industrial Park, Annfield plane, County Durham, DH9 7YB, UK) was washed with and without the Lento polypeptide. The soiled laundry items were cut in halves, except for the socks, and one half was washed with Lento and the other half without. The pairs of socks were split so that one sock of each pair was washed with Lento and the other without. To reduce the error of the following panel evaluation, the halves of each item were randomly divided between wash with or without Lento. This means that the left half of the items was not always washed with Lento. In each wash there were 2 half shirts, 2 half tea towels, one sock and 2 half T-shirts.

The items were washed in 50 mM $Na_2CO_3$ buffer, pH 7.7, or in a liquid detergent (Unilever, Via Sensitive Color, batch 60822 LN 06:23, bar code 7 31 0002 346246), dosage 6.7 g/L, water hardness 15° dH, $Ca^{2+}/Mg^{2+}$ ratio was 4:1, and the concentration of $NaHCO_3$ was 5 mM in the wash water. The detergent did not contain any perfume. The concentration of Lento was 0.76 mg enzyme protein/L wash water. The washes were conducted in Miele Softtronic W2245, program Mini with "vand plus" (extra water), totally 13 L wash water. Wash temperature was 40° C. In each wash, 5 pillowcases (100% polyester), 7 T-shirts (100% cotton), 3 shirts (65/35% polyester/cotton) and 1 tea towel (100% cotton) was used as ballast.

After wash, a panel of 7 persons individually evaluated the odor of the wet items. The panel did not know which one of the halves that had been washed with Lento. The odor was graded by a scale of 0-4 (see Table 3). If any difference between corresponding items (+/−treatment with Lento) had been identified, each panelist then specified which one of the items had the worst odor.

TABLE 3

Grades of odor evaluation

| Grade | Explanation |
|---|---|
| 0 | No difference between the two items |
| 1 | I think there is a difference between the two items |
| 2 | I know there is a difference between the two items |
| 3 | There is a clear difference between the two items |
| 4 | This item really smells worse than the other |

For each item, the mean value and the preference were calculated from the evaluation results as follows:

The mean value was calculated by adding all grades where the panelists had specified the item washed without Lento as the item with worst odor, and subtracting the grades where the panelists had specified the item washed with Lento as the item with worst odor. This sum was then divided by the number of panelists. The higher the mean value, the better was the smell reduction caused by Lento.

The preference was calculated by taking the number of panelists who specified items washed with Lento as having the lowest odor and dividing it by the total amount of panelists. This was then compared to the number of panelists that specified items washed without Lento as having the lowest odor, divided by the total amount of panelists. For example, in a case where the number of panelists that could not tell any difference in odor would be equally divided between the two samples, the preference would be 50%:50%.

The results from wash in buffer and liquid detergent are shown below in Tables 4 and 5, respectively.

TABLE 4

Results from wash in buffer

|  | Mean value | Preference (with Lento:without) |
|---|---|---|
| T-shirt 1 | 2.14 | 100%:0% |
| T-shirt 2 | 0.57 | 71%:29% |
| Sock | 1.57 | 86%:14% |
| Tea towel 1 | 0.43 | 64%:36% |
| Tea towel 2 | 0.57 | 64%:36% |
| Shirt 1 | −0.43 | 36%:64% |
| Shirt 2 | −0.43 | 43%:57% |
| Total | 0.63 | 66%:34% |

These results show that Lento has a reducing effect on the odor of the items, particularly on T-shirt 1 and the sock. Generally, the intensity varied a lot between the items, and items with low odor intensity were hard to evaluate, rendering results with ambiguous character. Mean values of these items are close to zero or preferences close to 50%:50%. This could be an explanation of the negative result for the two shirts. However, for the two items with strongest odor intensity, T-shirt 1 and the pair socks, Lento clearly had a positive effect.

TABLE 5

Results from wash in liquid detergent

|  | Mean value | Preference (with Lento:without) |
|---|---|---|
| T-shirt 1 | 0.57 | 71%:29% |
| T-shirt 2 | 0.29 | 57%:43% |
| Sock | 0.43 | 71%:29% |
| Tea towel 1 | −0.86 | 29%:71% |
| Tea towel 2 | 0.71 | 57%:43% |
| Shirt 1 | 0.14 | 50%:50% |
| Shirt 2 | −0.71 | 29%:71% |
| Total | 0.08 | 52%:48% |

These results show that Lento has an effect on odor reduction, also in the presence of detergents in particular for items with high odor intensity, as explained above.

The invention claimed is:

1. A method of killing and/or inhibiting growth of gram-positive bacterial cells comprising contacting the microbial cells with an antimicrobial polypeptide selected from the group consisting of:
   (a) a polypeptide with an amino acid sequence which has a degree of sequence identity to amino acids 1-85 of SEQ ID NO: 2 of at least 95%;
   (b) a polypeptide which is encoded by a nucleic acid sequence which hybridizes under medium stringency conditions with
      (i) nucleotides 124-378 of SEQ ID NO: 1,
      (ii) a subsequence of (i) of at least 100 nucleotides, or
      (iii) the full length complementary strand of (i) or (ii);
   wherein the medium stringency conditions comprise prehybridization and hybridization at 42° C. in 5×SSPE, 0.3% SDS, 200 micrograms/ml sheared and denatured salmon sperm DNA, and 35% formamide, following by washing three times each for 15 minutes using 2×SSC, 0.2% SDS at 55° C.; and
   (c) a fragment of the sequence of amino acids 1-85 of SEQ ID NO: 2, which has antimicrobial activity.

2. The method of claim 1, wherein the antimicrobial polypeptide is a polypeptide with an amino acid sequence which has a degree of sequence identity to amino acids 1-85 of SEQ ID NO: 2 of at least 95%.

3. The method of claim 1, wherein the antimicrobial polypeptide is a polypeptide with an amino acid sequence which has a degree of sequence identity to amino acids 1-85 of SEQ ID NO: 2 of at least 97%.

4. The method of claim 1, wherein the antimicrobial polypeptide is encoded by a nucleic acid sequence which hybridizes under medium stringency conditions with
   (a) nucleotides 124-378 of SEQ ID NO: 1,
   (b) a subsequence of (i) of at least 100 nucleotides, or
   (c) the full length complementary strand of (i) or (ii);
wherein the medium stringency conditions comprise prehybridization and hybridization at 42° C. in 5×SSPE, 0.3% SDS, 200 micrograms/ml sheared and denatured salmon sperm DNA, and 35% formamide, following by washing three times each for 15 minutes using 2×SSC, 0.2% SDS at 55° C.

5. The method of claim 1, wherein the antimicrobial polypeptide is encoded by a nucleic acid sequence which hybridizes under medium-high stringency conditions with
   (a) nucleotides 124-378 of SEQ ID NO: 1,
   (b) a subsequence of (i) of at least 100 nucleotides, or
   (c) the full length complementary strand of (i) or (ii);

wherein the medium-high stringency conditions comprise prehybridization and hybridization at 42° C. in 5×SSPE, 0.3% SDS, 200 micrograms/ml sheared and denatured salmon sperm DNA, and 35% formamide, following by washing three times each for 15 minutes using 2×SSC, 0.2% SDS at 60° C.

6. The method of claim 1, wherein the antimicrobial polypeptide is encoded by a nucleic acid sequence which hybridizes under high stringency conditions with
  (a) nucleotides 124-378 of SEQ ID NO: 1,
  (b) a subsequence of (i) of at least 100 nucleotides, or
  (c) the full length complementary strand of (i) or (ii);
wherein the high stringency conditions comprise prehybridization and hybridization at 42° C. in 5×SSPE, 0.3% SDS, 200 micrograms/ml sheared and denatured salmon sperm DNA, and 50% formamide, following by washing three times each for 15 minutes using 2×SSC, 0.2% SDS at 65° C.

7. The method of claim 1, wherein the antimicrobial polypeptide is encoded by a nucleic acid sequence which hybridizes under very high stringency conditions with
  (a) nucleotides 124-378 of SEQ ID NO: 1,
  (b) a subsequence of (i) of at least 100 nucleotides, or
  (c) the full length complementary strand of (i) or (ii);
wherein the very high stringency conditions comprise prehybridization and hybridization at 42° C. in 5×SSPE, 0.3% SDS, 200 micrograms/ml sheared and denatured salmon sperm DNA, and 50% formamide, following by washing three times each for 15 minutes using 2×SSC, 0.2% SDS at 70° C.

8. The method of claim 1, wherein the antimicrobial polypeptide is a fragment of amino acids 1-85 of SEQ ID NO: 2, which has antimicrobial activity.

* * * * *

SEQUENCE LISTING

```
<160> NUMBER OF SEQ ID NOS: 8

<210> SEQ ID NO 1
<211> LENGTH: 381
<212> TYPE: DNA
<213> ORGANISM: Bacillus licheniformis ATCC 14580
<220> FEATURE:
<221> NAME/KEY: CDS
<222> LOCATION: (1)..(378)
<220> FEATURE:
<221> NAME/KEY: mat_peptide
<222> LOCATION: (124)..(378)

<400> SEQUENCE: 1 atg aaa aat cat ttg tat gag aaa aaa aag agg aaa cct ttg act cgg      48
Met Lys Asn His Leu Tyr Glu Lys Lys Lys Arg Lys Pro Leu Thr Arg
    -40                 -35                 -30 aca att aaa gcg acg ctc gcc gtg ttg aca atg tcc atc gct ttg gtg      96
Thr Ile Lys Ala Thr Leu Ala Val Leu Thr Met Ser Ile Ala Leu Val
-25                 -20                 -15                 -10 gga ggc gct acg gtg cct tca ttt gca tgg gtg aat ccg ggt tat cac     144
Gly Gly Ala Thr Val Pro Ser Phe Ala Trp Val Asn Pro Gly Tyr His
```

```
                 -5              -1 1              5
tac cag tac cca tcg gaa ggt ggt aca tgg agg tat gga ttc gta aac    192
Tyr Gln Tyr Pro Ser Glu Gly Gly Thr Trp Arg Tyr Gly Phe Val Asn
         10                  15                  20 gcc ggg ctc cgt tca gag tac aac cac ccg aca aag gtc cac ggc tcg    240
Ala Gly Leu Arg Ser Glu Tyr Asn His Pro Thr Lys Val His Gly Ser
     25                  30                  35 aca gtg caa aag ctc atc gat gga aaa gtg gat aaa acg aat aga agt    288
Thr Val Gln Lys Leu Ile Asp Gly Lys Val Asp Lys Thr Asn Arg Ser
40                  45                  50                  55 att gat acg gct gcg ggc cgc tac tct aat gcc tat gtc gga gcc ata    336
Ile Asp Thr Ala Ala Gly Arg Tyr Ser Asn Ala Tyr Val Gly Ala Ile
                    60                  65                  70 aac tca cct ggt ctt aag ggt cgt tac tac tat cgc acc aac taa        381
Asn Ser Pro Gly Leu Lys Gly Arg Tyr Tyr Tyr Arg Thr Asn
            75                  80              85

<210> SEQ ID NO 2
<211> LENGTH: 126
<212> TYPE: PRT
<213> ORGANISM: Bacillus licheniformis ATCC 14580

<400> SEQUENCE: 2

Met Lys Asn His Leu Tyr Glu Lys Lys Arg Lys Pro Leu Thr Arg
    -40                 -35                 -30

Thr Ile Lys Ala Thr Leu Ala Val Leu Thr Met Ser Ile Ala Leu Val
-25                 -20                 -15                 -10

Gly Gly Ala Thr Val Pro Ser Phe Ala Trp Val Asn Pro Gly Tyr His
                -5              -1  1              5

Tyr Gln Tyr Pro Ser Glu Gly Gly Thr Trp Arg Tyr Gly Phe Val Asn
         10                  15                  20

Ala Gly Leu Arg Ser Glu Tyr Asn His Pro Thr Lys Val His Gly Ser
     25                  30                  35

Thr Val Gln Lys Leu Ile Asp Gly Lys Val Asp Lys Thr Asn Arg Ser
40                  45                  50                  55

Ile Asp Thr Ala Ala Gly Arg Tyr Ser Asn Ala Tyr Val Gly Ala Ile
                    60                  65                  70

Asn Ser Pro Gly Leu Lys Gly Arg Tyr Tyr Tyr Arg Thr Asn
            75                  80              85

<210> SEQ ID NO 3
<211> LENGTH: 10
<212> TYPE: PRT
<213> ORGANISM: Bacillus licheniformis ATCC 14580
<220> FEATURE:
<221> NAME/KEY: MISC_FEATURE
<223> OTHER INFORMATION: N-terminal

<400> SEQUENCE: 3

Trp Val Asn Pro Gly Tyr His Tyr Gln Tyr
1               5                   10

<210> SEQ ID NO 4
<211> LENGTH: 31
<212> TYPE: DNA
<213> ORGANISM: Artificial Sequence
<220> FEATURE:
<223> OTHER INFORMATION: Primer Pep 481
<220> FEATURE:
<221> NAME/KEY: misc_feature
<223> OTHER INFORMATION: Primer
```

```
<400> SEQUENCE: 4
aattacgcgt gttggtgcga tagtagtaac g                                    31

<210> SEQ ID NO 5
<211> LENGTH: 29
<212> TYPE: DNA
<213> ORGANISM: Artificial Sequence
<220> FEATURE:
<223> OTHER INFORMATION: Primer Pep 482
<220> FEATURE:
<221> NAME/KEY: misc_feature
<223> OTHER INFORMATION: Primer

<400> SEQUENCE: 5
ttaagaattc gaatgaaaga ggaggaatg                                       29

<210> SEQ ID NO 6
<211> LENGTH: 125
<212> TYPE: PRT
<213> ORGANISM: Bacillus licheniformis strain 009
<220> FEATURE:
<221> NAME/KEY: mat_peptide
<222> LOCATION: (41)..(125)

<400> SEQUENCE: 6

Met Lys Asn Leu Leu Asn Lys Lys Arg Lys Pro Leu Thr Arg Thr
-40                 -35                 -30                 -25

Ile Lys Ala Thr Phe Ala Val Leu Thr Val Ser Ile Gly Leu Val Gly
                -20                 -15                 -10

Gly Ala Thr Val Pro Ala Phe Ala Trp Val Asn Pro Asp Tyr His Tyr
                -5                  -1  1                   5

Gln Tyr Pro Ser Glu Gly Gly Thr Trp Arg Tyr Gly Phe Val Asn Leu
        10                  15                  20

Gly Leu Arg Ser Glu Tyr Asn His Pro Lys Lys Val His Gly Ser Thr
    25                  30                  35                  40

Val Gln Lys Leu Ile Asp Gly Lys Val Glu Lys Thr Asn Arg Ser Leu
                    45                  50                  55

Asp Thr Ala Pro Gly Arg Tyr Ser Asn Ala Tyr Val Gly Val Val Asn
            60                  65                  70

Ser Pro Gly Leu Lys Gly Arg Tyr Tyr Tyr Arg Thr Asn
        75                  80                  85

<210> SEQ ID NO 7
<211> LENGTH: 126
<212> TYPE: PRT
<213> ORGANISM: Bacillus licheniformis strain 470
<220> FEATURE:
<221> NAME/KEY: mat_peptide
<222> LOCATION: (42)..(126)

<400> SEQUENCE: 7

Met Lys Asn Tyr Leu Tyr Glu Lys Lys Arg Lys Pro Leu Thr Arg
                -40                 -35                 -30

Thr Ile Lys Ala Thr Leu Ala Val Leu Thr Met Ser Ile Ala Leu Val
-25                 -20                 -15                 -10

Gly Gly Ala Thr Val Pro Ala Phe Ala Trp Val Asn Pro Gly Tyr His
                    -5                  -1  1                   5

Tyr Gln Tyr Pro Ser Glu Gly Gly Thr Trp Arg Tyr Gly Phe Val Asn
        10                  15                  20

Ala Gly Leu Arg Ser Glu Tyr Asn His Pro Thr Lys Val His Gly Ser
    25                  30                  35
```

```
-continued

Thr Val Gln Lys Leu Ile Asp Gly Lys Val Asp Lys Thr Asn Arg Ser
40              45                  50                  55

Ile Asp Thr Ala Ala Gly Arg Tyr Ser Asn Ala Tyr Val Gly Ala Ile
                60                  65                  70

Asn Ser Pro Gly Leu Lys Gly Arg Tyr Tyr Tyr Arg Thr Asn
            75                  80              85

<210> SEQ ID NO 8
<211> LENGTH: 126
<212> TYPE: PRT
<213> ORGANISM: Artificial Sequence
<220> FEATURE:
<223> OTHER INFORMATION: Consensus sequence
<220> FEATURE:
<221> NAME/KEY: mat_peptide
<222> LOCATION: (42)..(126)

<400> SEQUENCE: 8

Met Lys Asn His Leu Tyr Glu Lys Lys Arg Lys Pro Leu Thr Arg
    -40             -35                 -30

Thr Ile Lys Ala Thr Leu Ala Val Leu Thr Met Ser Ile Ala Leu Val
-25             -20                 -15                 -10

Gly Gly Ala Thr Val Pro Ala Phe Ala Trp Val Asn Pro Gly Tyr His
                -5              -1  1                   5

Tyr Gln Tyr Pro Ser Glu Gly Thr Trp Arg Tyr Gly Phe Val Asn
            10              15              20

Ala Gly Leu Arg Ser Glu Tyr Asn His Pro Thr Lys Val His Gly Ser
    25                  30                  35

Thr Val Gln Lys Leu Ile Asp Gly Lys Val Asp Lys Thr Asn Arg Ser
40              45                  50                  55

Ile Asp Thr Ala Ala Gly Arg Tyr Ser Asn Ala Tyr Val Gly Ala Ile
                60                  65                  70

Asn Ser Pro Gly Leu Lys Gly Arg Tyr Tyr Tyr Arg Thr Asn
            75                  80              85
```